US00PP25814P2

(12) United States Plant Patent
Fisher

(10) Patent No.: US PP25,814 P2
(45) Date of Patent: Aug. 18, 2015

(54) ***MANDEVILLA* PLANT NAMED 'FGVR2'**

(50) Latin Name: *Mandevilla splendens*
Varietal Denomination: FGVR2

(75) Inventor: Wes Fisher, Sebring, FL (US)

(73) Assignee: Fury Genetics LLC, Hawthorne, FL (US)

( * ) Notice: Subject to any disclaimer, the term of this patent is extended or adjusted under 35 U.S.C. 154(b) by 44 days.

(21) Appl. No.: 13/573,171

(22) Filed: Aug. 27, 2012

(51) Int. Cl.
*A01H 5/02* (2006.01)

(52) U.S. Cl.
USPC ..... Plt./232

(58) Field of Classification Search
USPC ..... Plt./232
See application file for complete search history.

(56) References Cited

U.S. PATENT DOCUMENTS

| | | | | |
|---|---|---|---|---|
| PP19,698 | P2 * | 2/2009 | Fisher et al. | Plt./232 |
| PP20,777 | P2 * | 2/2010 | Brown | Plt./232 |
| PP22,543 | P2 * | 3/2012 | Kearley | Plt./232 |
| PP23,293 | P2 * | 1/2013 | Fisher et al. | Plt./232 |

* cited by examiner

*Primary Examiner* — Susan McCormick Ewoldt
(74) *Attorney, Agent, or Firm* — C. A. Whealy

(57) ABSTRACT

A new and distinct cultivar of *Mandevilla* plant named 'FGVR2', characterized by its upright, outwardly spreading and strongly vining plant habit; freely branching habit, dense and bushy appearance; medium green-colored leaves; numerous large dark red-colored flowers; and good garden performance.

2 Drawing Sheets

Botanical designation: *Mandevilla splendens.*
Cultivar denomination: 'FGVR2'.

BACKGROUND OF THE INVENTION

The present invention relates to a new and distinct cultivar of *Mandevilla* plant, botanically known as *Mandevilla splendens* and hereinafter referred to by the name 'FGVR2'.

The new *Mandevilla* plant is a naturally-occurring branch mutation of *Mandevilla splendens* 'DIP 79', disclosed in U.S. Plant Pat. No. 19,698. The new *Mandevilla* plant was discovered and selected by the Inventor on a single plant within a population of plants of 'DIP 79' grown in a controlled greenhouse environment in Sebring, Fla. on Jul. 9, 2008. The new *Mandevilla* plant was selected on the basis of its vining plant habit and flower color.

Asexual reproduction of the new *Mandevilla* plant by tip cuttings in a controlled greenhouse in Sebring, Fla. since Jul. 10, 2008 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'FGVR2'. These characteristics in combination distinguish 'FGVR2' as a new and distinct *Mandevilla* plant:

1. Upright, outwardly spreading and strongly vining plant habit.
2. Freely branching habit, dense and bushy appearance.

3. Medium green-colored leaves.
4. Numerous large dark red-colored flowers.
5. Good garden performance.

Plants of the new *Mandevilla* differ primarily from plants of the parent, 'DIP 79', in the following characteristics:

1. Plants of the new *Mandevilla* are more strongly vining than plants of 'DIP 79'.
2. Plants of the new *Mandevilla* and 'DIP 79' differ slightly in flower color as plants of 'DIP 79' have lighter red-colored flowers.

Plants of the new *Mandevilla* can be compared to plants of *Mandevilla hybrida* 'FGVP1', disclosed in U.S. Plant patent application Ser. No. 13/573,172. Plants of the new *Mandevilla* differ primarily from plants of 'FGVP1' in flower color as plants of 'FGVP1' have pink-colored flowers. In addition, in side-by-side comparisons, plants of the new *Mandevilla* are more vigorous than plants of 'FGVP1'.

Plants of the new *Mandevilla* can be compared to plants of *Mandevilla hybrida* 'FG1PK', disclosed in U.S. Plant Pat. No. 22,543. Plants of the new *Mandevilla* differ primarily from plants of 'FG1PK' in flower color as plants of 'FG1PK' have marbled red purple and light red purple-colored flowers. In addition, in side-by-side comparisons, plants of the new *Mandevilla* are more vigorous than plants of 'FG1PK'.

Plants of the new *Mandevilla* can be compared to plants of *Mandevilla hybrida* 'FGDIP1RV', disclosed in U.S. Plant Pat. No. 23,293. Plants of the new *Mandevilla* differ primarily from plants of 'FGDIP1RV' in leaf color as plants of 'FGDIP1RV' have green, yellow green and pale yellow variegated leaves. In addition, in side-by-side comparisons, plants of the new *Mandevilla* are more vigorous than plants of 'FGDIP1RV'.

Plants of the new *Mandevilla* can also be compared to plants of the *Mandevilla hybrida* 'Audrey', disclosed in U.S. Plant Pat. No. 20,777. In side-by-side comparisons conducted in Sebring, Fla., plants of the new *Mandevilla* differed from plants of 'Audrey' in the following characteristics:

1. Plants of the new *Mandevilla* were more strongly vining than plants of 'Audrey'.
2. Plants of the new *Mandevilla* had shorter internodes than plants of 'Audrey'.
3. Leaves of plants of the new *Mandevilla* were smaller than leaves of plants of 'Audrey'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'FGVR2' grown in a container.

The photograph on the second sheet is a close-up view of a typical flowering plant of 'FGVR2'.

DETAILED BOTANICAL DESCRIPTION

Plants used for the aforementioned photographs and following description were grown during the spring and summer in 2-gallon containers in an outdoor nursery in Fort Worth, Tex. and under cultural practices which closely approximate commercial production conditions. During the production of the plants, day temperatures ranged from 24° C. to 38° C. and night temperatures ranged from 21° C. to 24° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla splendens* 'FGVR2'.

Parentage: Naturally-occurring branch mutation of *Mandevilla splendens* 'DIP 79', disclosed in U.S. Plant Pat. No. 19,698.

Propagation:

*Type.*—By tip cuttings.

*Time to initiate roots, summer.*—About 14 to 16 days at 29° C. to 32° C.

*Time to initiate roots, winter.*—About 17 to 18 days at 24° C.

*Time to produce a rooted young plant, summer.*—About 35 days at 29° C. to 32° C.

*Time to produce a rooted young plant, winter.*—About 45 days at 24° C.

*Root description.*—Fibrous to fleshy, medium in thickness; white in color.

*Rooting habit.*—Moderately freely branching; medium density.

Plant description:

*Plant and growth habit.*—Upright, outwardly spreading and strongly vining plant habit; vigorous growth habit; freely branching habit; dense and bushy appearance.

*Vine length.*—About 120 cm to 180 cm.

*Plant diameter (spread).*—About 54 cm to 76 cm.

*Lateral branch description.*—Length: About 60 cm to 110 cm. Diameter: About 3.5 mm. Internode length: About 5 cm to 12 cm. Strength: Flexible, strong. Texture, young stems: Smooth. Texture, developed stems: Woody. Color, young stems: Close to 175A. Color, woody stems: Close to 183A.

Leaf description:

*Arrangement.*—Opposite, simple.

*Length.*—About 5.25 cm.

*Width.*—About 3 cm.

*Shape.*—Elliptic to ovate.

*Apex.*—Cuspidate.

*Base.*—Cuneate with obtuse tendencies.

*Margin.*—Entire.

*Texture, upper and lower surfaces.*—Smooth, glabrous.

*Venation pattern.*—Pinnate.

*Color.*—Developing leaves, upper surface: Close to 146A; midvein and margins, close to 53A. Developing leaves, lower surface: Close to 146B; midvein and margins, close to 53A to 53B. Fully expanded leaves, upper surface: Close to N137A to N137B; venation, close to 144A. Fully expanded leaves, lower surface: Close to 146B; venation, close to 154D.

*Petioles.*—Length: About 1.2 cm to 2 cm. Diameter: About 2.5 mm. Texture, upper and lower surfaces: Smooth, glabrous. Color, upper and lower surfaces: Close to 144A to 144B.

Flower description:

*Flower type and habit.*—Single salverform flowers; flowers arranged in terminal and axillary clusters; flowers face mostly outwardly; freely flowering habit.

*Natural flowering season.*—Plants of the new *Mandevilla* flower continuously year-round in Florida.

*Flower longevity on the plant.*—Flowers last about seven to nine five days; flowers not persistent.

*Fragrance.*—Faint, mint-like.

*Flowers.*—Appearance: Flared trumpet, corolla fused, five-parted; flowers salverform and roughly star-shaped. Diameter: About 7.5 cm to 9 cm. Depth (length): About 5.5 cm. Throat diameter: About 1.75 cm. Tube length: About 5 cm. Tube diameter, base: About 3 mm.

*Flower buds.*—Length: About 3.1 cm. Diameter: About 4 mm. Shape: Cylindrical, pointed. Color: Towards the base, close to 144A; towards the apex, close to 60A.

*Corolla.*—Arrangement: Single whorl of five petals, fused into flared trumpet. Petal lobe length: About 3 cm. Petal lobe width: About 2.3 cm. Petal lobe shape: Roughly spatulate; asymmetrical. Petal apex: Obtuse and cuspidate. Petal margin: Entire. Petal texture, upper and lower surfaces: Smooth, glabrous; velvety. Throat and tube texture: Smooth, glabrous. Color: Petal, when opening, upper surface: Close to between 46A and 53A. Petal, when opening, lower surface: Close to 53A. Petal, fully opened, upper surface: Close to 53A; venation, close to 53A; color becoming closer to 61B with development. Petal, fully opened, lower surface: Close to 53A; venation, close to 53A. Throat: Close to 23A; towards the petal lobes, close to 53A; venation, close to 53A. Tube: Close to 4D heavily overlain with close to between 53A and 61B; at constriction point, close to 4D; towards the base, close to 46A.

*Sepals.*—Arrangement and appearance: Five per flower in a single whorl; fused towards the base. Length: About 1 cm. Width: About 2.5 mm. Shape: Lanceolate. Apex: Acute; slightly reflexed. Margin:

Entire. Texture, inner and outer surfaces: Smooth, glabrous. Color, inner surface: Close to 145B; towards the apex, close to 45A to 45B. Color, outer surface: Close to 144B; towards the apex, close to 45A to 45B.

*Peduncles.*—Length: About 1.4 cm. Diameter: About 2.5 mm. Texture: Smooth, glabrous. Strength: Flexible, but strong. Color: Close to 175A to 175B.

*Reproductive organs.*—Stamens: Quantity and arrangement: Typically five; filaments fused to corolla; anthers, connivent. Filament length: About 1.1 cm. Filament color: Close to 155D. Anther shape: Elongated oblong. Anther length: About 8 mm. Anther color: Close to 12A. Pollen amount: None observed. Pistils: Quantity: Typically one. Pistil length: About 1.75 cm. Stigma shape: Oblong to rounded. Stigma color: Close to 11D. Style length: About 1.4 cm. Style color: Close to 155D. Ovary color: Close to 145A to 145B.

*Seeds and fruits.*—Seed and fruit production have not been observed on plants of the new *Mandevilla*.

Disease & pest resistance: Plants of the new *Mandevilla* have not been observed to resistant to pathogens and pests common to *Mandevilla* plants.

Temperature tolerance: Plants of the new *Mandevilla* have been observed to tolerate temperatures from about 1° C. to about 40° C.

It is claimed:

1. A new and distinct *Mandevilla* plant named 'FGVR2' as illustrated and described.

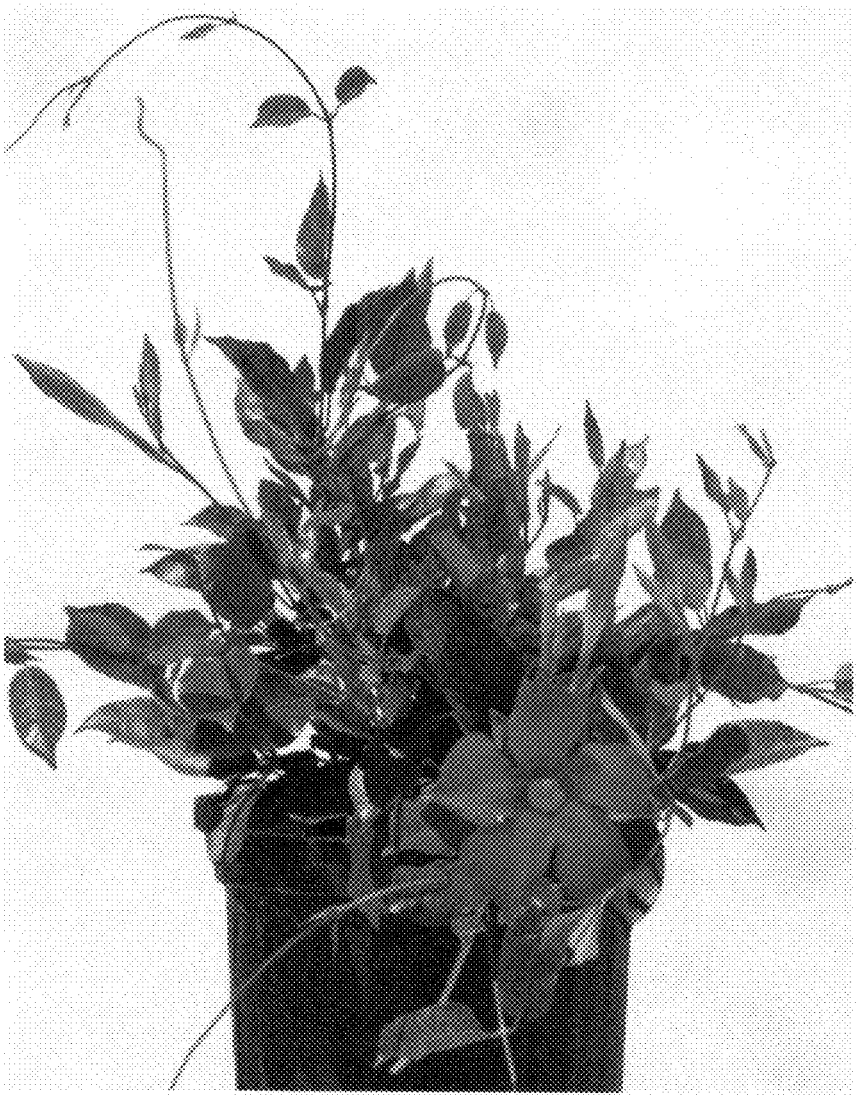

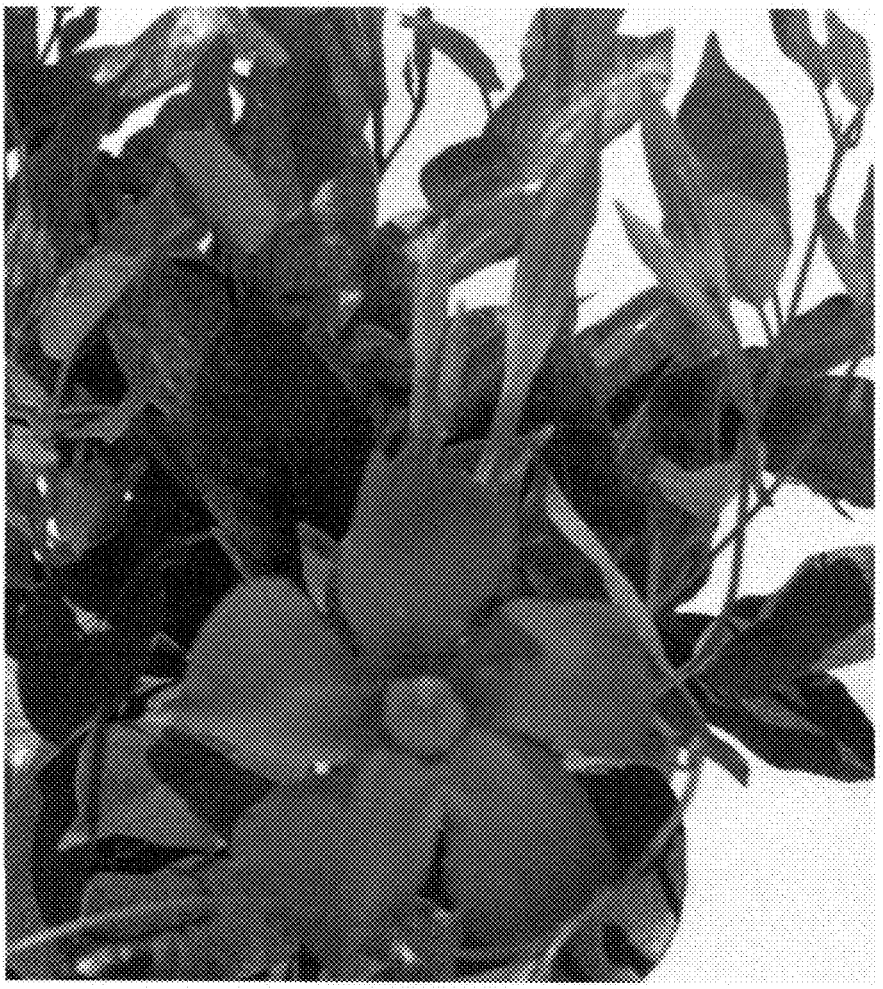

* * * * *